(12) United States Patent
Sacco

(10) Patent No.: US 8,791,322 B2
(45) Date of Patent: Jul. 29, 2014

(54) ABSORBENT SHEETS

(76) Inventor: Elizabeth Sacco, Middleton, MA (US)

( * ) Notice: Subject to any disclaimer, the term of this patent is extended or adjusted under 35 U.S.C. 154(b) by 441 days.

(21) Appl. No.: 13/308,050

(22) Filed: Nov. 30, 2011

(65) Prior Publication Data

US 2013/0138067 A1   May 30, 2013

(51) Int. Cl.
   *A61F 13/00*   (2006.01)
(52) U.S. Cl.
   CPC . *A61F 13/00029* (2013.01); *A61F 2013/00608* (2013.01)
   USPC ........................................ 604/378
(58) Field of Classification Search
   CPC ............... A61F 13/00029; A61F 2013/00438; A61F 2013/00604; A61F 2013/00608
   USPC ........ 604/360, 378, 385.02, 385.14; 600/316, 600/347, 362, 364
   See application file for complete search history.

(56) References Cited

U.S. PATENT DOCUMENTS

| | | | |
|---|---|---|---|
| 2,897,108 A | 7/1959 | Harwood | |
| 4,231,357 A | 11/1980 | Hessner | |
| 4,650,706 A * | 3/1987 | Emmel | 428/40.1 |
| 4,837,062 A * | 6/1989 | Dunshee et al. | 428/41.3 |
| 5,683,354 A | 11/1997 | Levy | |
| 5,939,339 A | 8/1999 | Delmore et al. | |
| 5,947,917 A | 9/1999 | Carte et al. | |
| 6,566,577 B1 | 5/2003 | Addison et al. | |
| 6,743,964 B2 | 6/2004 | Yoshida et al. | |
| 6,916,967 B2 | 7/2005 | Wright et al. | |
| 7,217,259 B2 * | 5/2007 | McDaniel | 604/385.17 |
| 7,396,976 B2 | 7/2008 | Hurwitz et al. | |
| 7,559,159 B1 * | 7/2009 | Lundberg | 36/73 |
| 7,753,204 B2 * | 7/2010 | Grossman | 206/440 |
| 7,922,036 B2 | 4/2011 | Bendor et al. | |
| 2003/0045852 A1 * | 3/2003 | Esselburn | 604/385.14 |
| 2003/0127352 A1 | 7/2003 | Buschkiel et al. | |
| 2006/0062956 A1 | 3/2006 | Chandaria et al. | |
| 2008/0027366 A1 | 1/2008 | Da Silva Macedo, Jr. | |
| 2008/0202952 A1 | 8/2008 | Rowe | |
| 2009/0157033 A1 | 6/2009 | Toro et al. | |
| 2011/0264068 A1 * | 10/2011 | Suga | 604/385.14 |

* cited by examiner

*Primary Examiner* — Lynne Anderson
(74) *Attorney, Agent, or Firm* — Lambert & Associates; Gary E. Lambert; David J. Connaughton, Jr.

(57) ABSTRACT

A fluid absorption device is provided. The device having a plurality of absorbent sheets. The absorbent sheets formed in a stack and removably attached to each other by an adhesive. The sheets are designed to be removed from each other one at a time for use in the absorption of fluids.

19 Claims, 2 Drawing Sheets

ABSORBENT SHEETS

BACKGROUND OF THE INVENTION

1. Field of the Invention

The present invention relates generally to absorbent sheets. More particularly, the present invention relates to a plurality of absorbent sheets removably attached to each other.

2. Description of Related Art

Absorbent sheets such as tissues may be employed for a number of uses including cleaning up small fluid spills, absorbing bodily fluid, blowing one's nose, and the like.

One particular application of absorbent sheets is to absorb blood from one's skin after a needle prick. However, typically the absorbent sheets used are unnecessarily large, cumbersome, and not transportable.

Moreover, travel sized absorbent sheet packs known in the art suffer from being inconvenient to dispense, and are cumbersome, especially for uses other than blowing one's nose. These travel sized sheet packs are, in many cases, larger than desirable.

Therefore, what is needed is a device that may provide compact absorbent sheet storage that may allow easy dispensing of the sheets.

SUMMARY OF THE INVENTION

The subject matter of this application may involve, in some cases, interrelated products, alternative solutions to a particular problem, and/or a plurality of different uses of a single system or article.

In one aspect, a fluid absorption device is provided. The device comprises a plurality of absorbent sheets organized in a stack. Each of the plurality of absorbent sheets is removably attached to another sheet by an adhesive disposed on or between each of the plurality of sheets.

In another aspect, a fluid absorption device is provided. The device comprises a plurality of absorbent sheets organized as a stack. Each of the sheets may have a reinforced region about at least part of a perimeter of the sheet. An adhesive disposed on or between each of the sheets allows the sheets to be removably attached to one another, wherein the sheets may be removed one at a time from a top of the stack.

DETAILED DESCRIPTION

Figure 1:
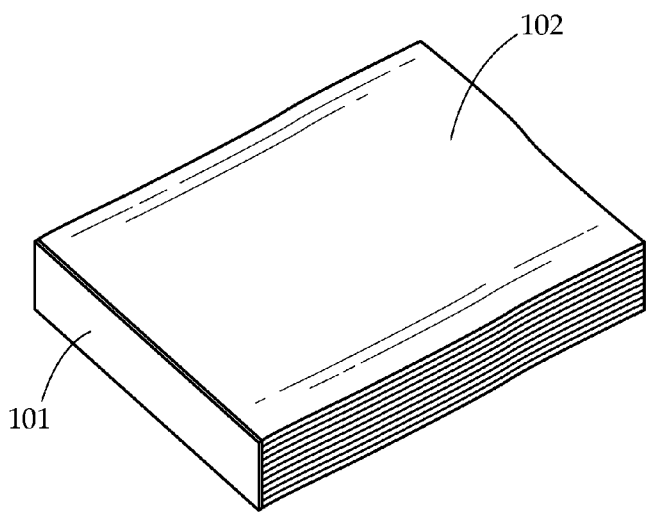
FIG. 1 provides a perspective view of one embodiment of the device.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

Generally, the present invention concerns a device comprising a plurality of absorbent sheets removably attached to each other in a stacked configuration, one sheet on top of another. The sheets are constructed and arranged to be removable, one or more at a time, from the rest of the plurality of sheets. This configuration thereby allows absorbent sheets of any size to be easily accessed for use.

The absorbent sheet may be constructed of any material or materials that can be formed into a sheet, with at least a portion of the sheet being absorbent. The sheet may vary in thickness depending on its intended application. In one embodiment, the absorbent sheet may be constructed of a tissue material. In another embodiment, the absorbent sheet may be constructed of paper-towel material. In still another embodiment, the absorbent sheet may be constructed of a thin absorbent cloth. In yet another embodiment, the absorbent sheet may be formed by absorbent synthetic fibers.

The absorbent sheet itself, as well as the plurality of absorbent sheets adhered together may be of any size and shape that may allow removal of one sheet from the plurality of sheets attached to each other. In one embodiment, the sheet may be sized to fit in a pocket of a user. In another embodiment, the sheet may be sized to fit conveniently on an office desk or dashboard of a vehicle. In still another embodiment, the sheet may be sized to fit conveniently within a blood glucose meter pack.

It should be understood that the absorbent sheets may be formed in any shape desirable. In one embodiment, the absorbent sheets may be formed in a rectangular shape. In another embodiment, the absorbent sheets may be rounded.

The device may comprise a quantity of adhesive disposed on or between each of the sheets. The adhesive may be configured to allow the plurality of sheets to be attached to one another. The adhesive may also allow the tissue sheets to be removed from each other without substantial difficulty or substantial damage to the sheet being removed. Thus the adhesive preferably may be strong enough to maintain an attachment of each of the plurality of absorbent sheets but not so strong as to prevent the removal of one of the sheets without damage or difficulty. In one embodiment, the adhesive may be a substance that is not toxic to humans.

In one embodiment, the adhesive may be disposed on a top back surface of an absorbent sheet. The top back surface may then be adhered to a top front surface of another absorbent sheet. In a further embodiment, this may be repeated for a plurality of sheets, thereby forming a stack of the sheets.

In another embodiment, the adhesive may be coated along a top edge of a sheet. This embodiment may any adhesive that may be coated along a top of a plurality of the adhesive sheets when the sheets are arranged in a stack.

In a further embodiment, the absorbent sheet may have a second material different from the absorbent material attached to it. The second material may serve as an adhesion section. The adhesion section may be any material suitable for receiving the adhesive that may facilitate removal of the absorbent sheet from another absorbent sheet.

In one embodiment, the adhesion section may be a smooth plastic strip. In this embodiment, the absorbent sheet may be attached to the plastic strip. The adhesive may be disposed on a portion of the plastic strip which may then be attached to a plastic strip adhesion section of another absorbent sheet.

In another embodiment, the adhesion section may be a section of paper thicker and less absorbent than the absorbent sheet. In this embodiment, the absorbent sheet may be attached to the adhesion section. The adhesive may be disposed on a portion of the adhesion section, which may then be attached to an adhesion section of another absorbent sheet.

In further embodiments, the separate material of the adhesion section may serve as a handle to aid in holding and manipulating the sheet and the sheet's absorbent portion.

The device may further comprise a backing sheet attached to a bottom-most absorbent sheet. In one embodiment, the backing sheet may be constructed of a material different from the absorbent sheets. For example, the backing sheet may be non-absorbent. In some embodiments, the backing sheet may be a plastic sheet or paper sheet. The backing sheet may provide a supportive base for the tissues to attach to.

A securing device may be attached to the backing sheet in some embodiment. The securing device is configured to allow the device to be adhered or otherwise secured to a surface. This securing device may be any device or structure that may allow attachment or other securing of the plurality of absorbent sheets to a surface. In one embodiment, the securing device may be an adhesive. In another embodiment, the securing device may be a Velcro® type hook-and-loop fastening system. In still another embodiment, a snap in structure may allow the sheets and securing device to snap into a receiver.

The absorbent sheets may further comprise a reinforcement portion. The reinforcement portion may prevent the absorbent sheets from ripping or being otherwise damaged from tensile, shearing, and other forces applied to a sheet during removal from another of the absorbent sheets. The reinforcement may be any structure that may reinforce the sheets. In one embodiment, the reinforcement may be positioned on one edge of a sheet. In another embodiment, the reinforcement may be positioned about multiple edges of a sheet.

In one embodiment, the reinforcement may be a folded region of the absorbent sheet, the folded region forming a thicker, multi-ply region that is more resistant to damage when under sheet removal forces.

In another embodiment, the reinforcement may be a thin strip of durable material positioned on an edge of a sheet. Examples of thin durable materials may include plastic, paper or metal strips. This material may be adhered, integrated, or otherwise formed to the absorbent sheet.

In yet another embodiment, the reinforcement may be formed as a dried liquid substance applied to an edge of the absorbent sheet. For example a liquid substance may be disposed on an edge of a sheet. This liquid may be absorbed by the absorbent sheet and may dry to a state that provides the sheet and dried substance more durability than the sheet alone.

The device contemplated herein may further comprise packaging. The packaging may be any structure that at least partially contains and protects the absorbent sheets.

In one embodiment, the packaging may be a plastic film that surrounds the sheets. In another embodiment, the packaging may be a flap connected to the backing sheet. The flap may be placed over the absorbent sheets in a first position, and placed away from the sheets, allowing access to the sheets in a second position.

The absorbent sheet may further comprise a quantity of antiseptic, aromatic, or otherwise therapeutic substance. In one embodiment, the substance may be antiseptic to disinfect a surface upon which the sheet is used. For example, when absorbing small quantities of blood, the antiseptic substance may disinfect the surface, thereby limiting infection.

In another embodiment, the substance may be aromatic to provide a pleasant aroma when using the absorbent sheet.

The present invention may be particularly applicable in conditions where easy access to absorbent sheets is desirable. The following are provided as non limiting examples only.

In one embodiment, the present invention may be incorporated into a blood glucose meter pack used by diabetics. The present invention may be conveniently located within the pack, and may be used to absorb blood from a needle prick required during blood glucose metering.

In another embodiment, the present invention may be positioned on a desk. The absorbent sheets may be sized to fit easily on a desk and to be useful for blowing ones nose, makeup application, spill cleanup, and the like.

In still another embodiment, the present invention may be attachable to a dashboard or other surface of a vehicle's interior. In this embodiment, the present invention may provide easy access to absorbent sheets while a driver is driving.

In yet another embodiment, the present invention may be utilized at nail salons for nail or toe polish applications. The present invention may be sized for nail salon use and may provide easy, one handed access to the absorbent sheet.

The present invention may be manufactured in any number of manners. In one embodiment, the plurality of sheets may be manufactured in a large sheet, and may be cut to a desired size and shape. In a further embodiment, the cut sheets may then be layered on top of one another, and the adhesive may be coated across a top edge of each sheet in the stacked layer.

In another embodiment, the plurality of sheets may be manufactured in a sheet and may be cut into the desired size and shape. In a further embodiment, the cut sheets may have a reinforcement applied to one or more edges of each sheet.

In still another embodiment, the plurality of sheets, after being manufactured in a large sheet and cut, may have an adhesive disposed on a rear top portion. After the adhesive is applied, the sheets may be layered on top of one another and adhered to each other, forming a stack.

Turning now to FIG. 1 a perspective view of one embodiment of the device is provided. Absorbent sheets 102 are substantially rectangular in shape. A plurality of these absorbent sheets 102 are stacked on top of each other. A quantity of adhesive 101 is disposed along a top edge of each of the plurality of adhesive sheets 102. The adhesive 101 allows the absorbent sheets 102 to be removably attached to one another and allows them to maintain their stacked configuration.

Figure 2:
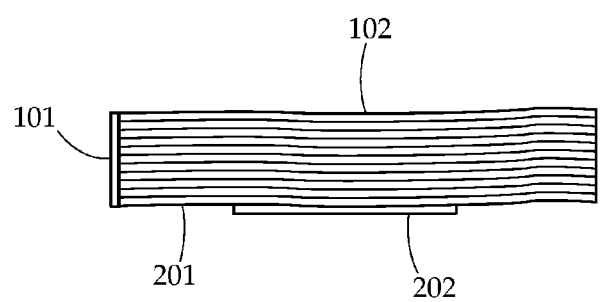
FIG. 2 provides a side view of another embodiment of the device.

FIG. 2 shows a side view of another embodiment of the device. In this view, the plurality of absorbent sheets 102 can be seen attached together by an adhesive 101. At a bottom-most layer of the adhesive sheets 102 is a backing sheet 201. The backing sheet 201 is constructed of a material different from the absorbent sheets 102. A pad 202 is attached to the backing sheet 201. The pad 202 comprises an adhesive on its bottom surface which allows the device to be securely attached to a surface.

Figure 3:
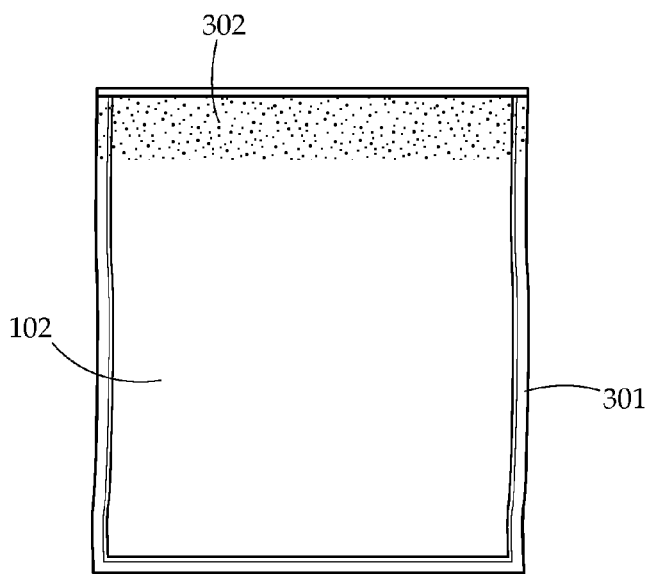
FIG. 3 provides a rear view of an embodiment of an absorbent sheet.

FIG. 3 provides a rear view of another embodiment of an absorbent sheet of the device. The absorbent sheet 102 comprises a reinforced region 301 that reinforces the edge of the absorbent sheet 102. An adhesive 302 is disposed on a top rear portion of the absorbent sheet 102.

The embodiment shown in this view may be placed upon another similarly configured absorbent sheet (not shown) and the adhesive 302 may adhere to a front top portion of the other adhesive sheet (not shown). In this manner, the sheets may be arranged in a stack, front to back.

Figure 4:
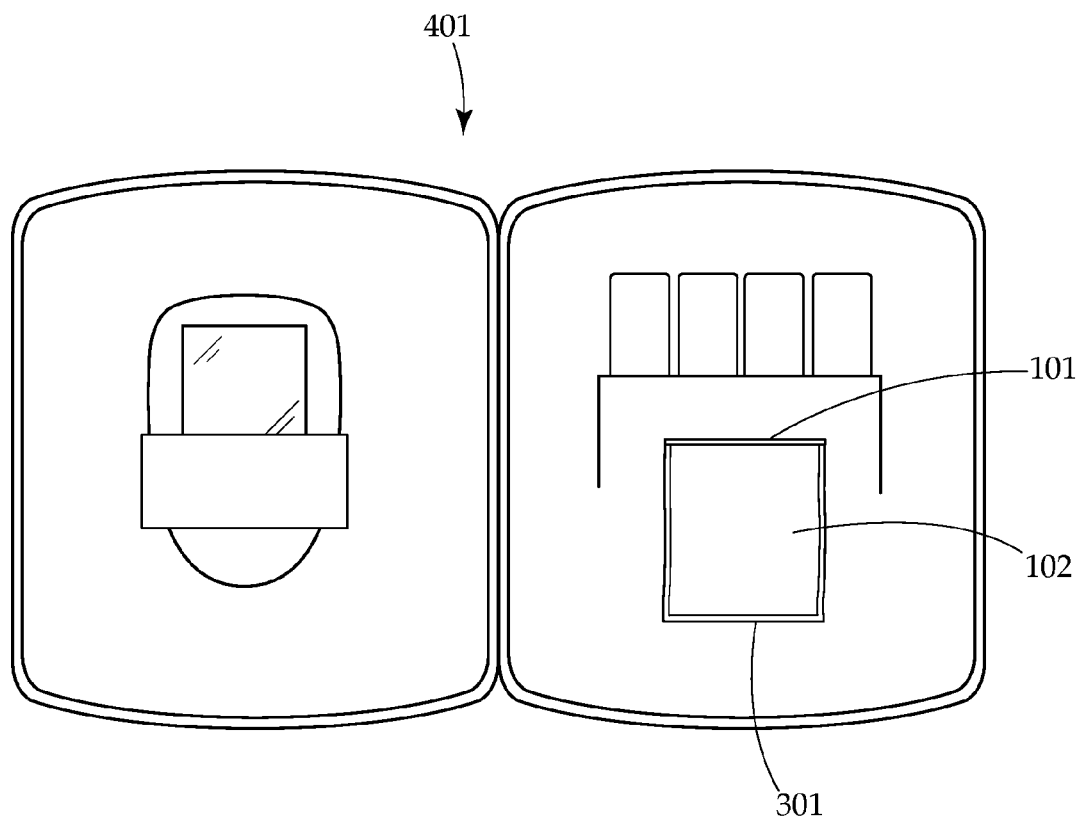
FIG. 4 provides a view of the present invention incorporated with a blood glucose test pack.

FIG. 4 provides a view of the present invention incorporated with a blood glucose test pack 401. The absorbent sheets 102 are attached to the diabetes test pack by a securing device (not shown). The absorbent sheets 102 are attached to each other by an adhesive 101. A reinforcement 301 is disposed around and edge of absorbent sheets 102. In this embodiment, a single absorbent sheet 102 may be easily accessed for absorption and cleanup of fluids such as blood from a needle prick caused by blood glucose testing.

Figure 5:
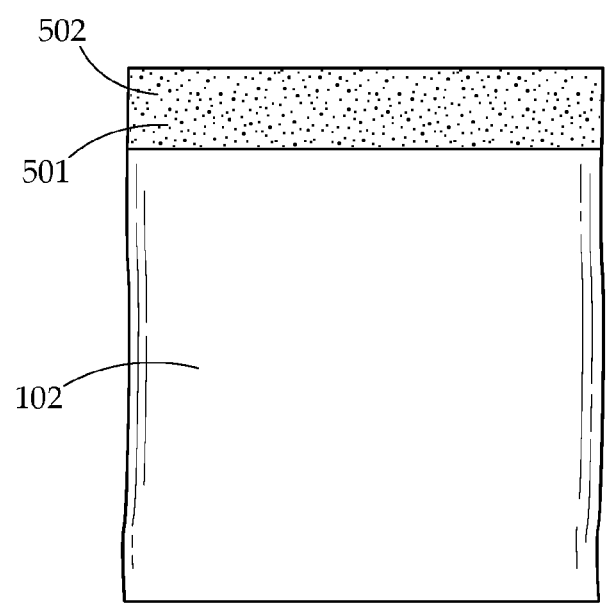
FIG. 5 provides a rear view of another embodiment of the absorbent sheet.

FIG. 5 provides a rear view of another embodiment of the absorbent sheet of the device. The adhesive sheet 102 has an adhesion section 501. The adhesion section 501 may be a different material than the absorbent sheet 102. Adhesive 502 is disposed on the adhesion section 501, allowing the absorbent sheet to be attached to another absorbent sheet (not shown) at an opposite side of its adhesion section.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. A fluid absorption device comprising:
a plurality of absorbent sheets, each absorbent sheet comprising a single layer of absorbent material, the plurality of absorbent sheets formed in a stack, at least part of the single layer of one of the plurality of absorbent sheets layered directly on top of the single layer of another of the plurality of absorbent sheets, and each of the plurality of absorbent sheets being removably attached to another of the plurality of absorbent sheets;
an adhesive disposed on a part of each of the plurality of absorbent sheets, the adhesive providing the removable attachment of the plurality of absorbent sheets; and
wherein each of the plurality of absorbent sheets is removable one absorbent sheet at a time from a top of the stack.

2. The fluid absorption device of claim 1 wherein at least one of the plurality of absorbent sheets further comprises a reinforcement disposed on an edge.

3. The fluid absorption device of claim 1 wherein each of the plurality of absorbent sheets further comprises a reinforcement disposed on an edge.

4. The fluid absorption device of claim 2 wherein the reinforcement is a folded region of the at least one of the plurality of absorbent sheets.

5. The fluid absorption device of claim 2 wherein the reinforcement is a strip of reinforcing material disposed on a surface of the at least one of the plurality of absorbent sheets.

6. The fluid absorption device of claim 1 wherein the plurality of absorbent sheets further comprises an adhesive disposed on a rear upper portion of each of the plurality of absorbent sheets.

7. The fluid absorption device of claim 1 wherein the adhesive is disposed over a top edge of each of the plurality of absorbent sheets.

8. The fluid absorption device of claim 1 further comprising a backing sheet attached on a back of a bottom-most absorbent sheet of the plurality of absorbent sheets, the backing sheet being constructed of a material sturdier than a material forming the plurality of absorbent sheets.

9. The fluid absorption device of claim 8 further comprising an attachment device constructed and arranged to attach the backing to a surface.

10. The fluid absorption device of claim 9 wherein the attachment device is a two-sided adhesive strip.

11. The fluid absorption device of claim 9 wherein the attachment device is a hook-and-loop device.

12. The fluid absorption device of claim 1 wherein each of the plurality of absorbent sheets further comprises an adhesion section comprised of a different material from an absorbent sheet material.

13. The fluid absorption device of claim 1 wherein each of the plurality of sheets comprises a quantity of antiseptic substance.

14. The fluid absorption device of claim 1 further comprising a removable cover partially surrounding the plurality of absorbent sheets.

15. A fluid absorption device comprising:
a plurality of absorbent sheets, each absorbent sheet comprising a single layer of absorbent material, the plurality of absorbent sheets formed in a stack, at least part of the single layer of one of the plurality of sheets layered directly on top of the single layer of another of the plurality of sheets, each of the plurality of absorbent sheets removably attached to another of the plurality of absorbent sheets, and each of the plurality of absorbent sheets further comprises a reinforced region about at least part of a sheet perimeter;
an adhesive disposed on a part of each of the plurality of absorbent sheets;
wherein each of the plurality of absorbent sheets is removable one absorbent sheet at a time from a top of the stack.

16. The fluid absorption device of claim 15 wherein the reinforced region comprises a multiple-layered absorbent sheet.

17. The fluid absorption device of claim 15 further comprising an attachment device attached to a bottom of the device constructed and arranged to allow attachment of the device to a surface.

18. The fluid absorption device of claim 15 wherein the adhesive is disposed on a rear upper portion of each of the plurality of absorbent sheets.

19. The fluid absorption device of claim 15 wherein the adhesive is disposed over a top edge of each of the plurality of absorbent sheets.

* * * * *